United States Patent
Hanna

[11] Patent Number: 5,944,731
[45] Date of Patent: Aug. 31, 1999

[54] SURGICAL APPLIANCE FOR SLICING A SLIVER FROM THE CORNEA

[76] Inventor: Khalil Hanna, 5 rue Cognacq-Jay 75007, Paris, France

[21] Appl. No.: 09/128,659

[22] Filed: Aug. 4, 1998

[30]  Foreign Application Priority Data

Aug. 5, 1997 [FR] France ................................. 97 10021

[51] Int. Cl.⁶ ...................................................... A61F 9/00
[52] U.S. Cl. .......................... 606/166; 606/167; 606/172; 606/174
[58] Field of Search ............................. 606/167, 166–170, 606/171, 172, 173, 174

[56]  References Cited

U.S. PATENT DOCUMENTS

| Re. 35,421 | 1/1997 | Ruiz et al. ............................... 606/166 |
| 4,326,529 | 4/1982 | Doss et al. ............................... 606/166 |
| 4,662,370 | 5/1987 | Zeiss . |
| 5,063,942 | 11/1991 | Kilmer et al. . |
| 5,312,428 | 5/1994 | Lieberman .............................. 606/166 |
| 5,318,044 | 6/1994 | Kilmer et al. . |
| 5,368,604 | 11/1994 | Kilmer et al. . |
| 5,395,385 | 3/1995 | Kilmer et al. . |
| 5,591,185 | 1/1997 | Kilmer et al. . |
| 5,624,456 | 4/1997 | Hellenkamp . |

Primary Examiner—Michael Buiz
Assistant Examiner—Lien Ngo
Attorney, Agent, or Firm—Griffin, Butler, Whisenhunt & Szipl, LLP

[57]  ABSTRACT

A surgical appliance for slicing a sliver from the cornea comprises:
- a base comprising an annular suction chamber shaped to be pressed against the sclera of an eye;
- a cornea-shaping element situated above the base and having a surface turned to face it; and
- a cutting blade movable in a plane that is situated between the surface of the shaping element, and the base.

According to the invention, the appliance has a general support to which the base is coupled by means enabling its position relative to the support to be adjusted along the axis of symmetry of the annular chamber, and to which the cutting blade is coupled by means enabling its position relative to the general support to be adjusted along a direction parallel to the axis of symmetry of the annular chamber and enabling it to be displaced perpendicularly to said axis.

12 Claims, 7 Drawing Sheets

FIG_1

FIG_2

FIG_3

FIG_5

FIG_6

SURGICAL APPLIANCE FOR SLICING A SLIVER FROM THE CORNEA

The present invention relates to a surgical appliance (or "keratome") for surgery of the cornea, and more particularly for slicing a sliver from the cornea.

BACKGROUND OF THE INVENTION

Amongst refractive surgical techniques (surgery of the cornea) seeking to correct ametropia, one of the known techniques is derived from the technique developed by Jose Barraquer and known as in situ keratomileusis. It consists in slicing a disk from the cornea by means of a microkeratome. The disk is raised, after which a small lens is removed from the plane uncovered by raising the disk, where the thickness and the dimensions of the small lens are a function of the correction to be provided. Thereafter, the disk of cornea is replaced on the plane that has been modified in this way, thus giving rise to a modification to the front surface of the cornea, and hence modifying its optical characteristics.

Interest in that technique has recently been renewed by use of the excimer laser which makes it possible to remove tissue extremely precisely. This has made it possible to control the dimensions of the small lenses in very much finer manner than with the previously used mechanical means.

In this type of surgery, the disk is removed by means of a microkeratome, i.e. a tool that is similar to a miniature plane having a blade that vibrates in the direction of its cutting edge, and the depth of cut is adjusted by means of wedges of precalibrated thickness or by micrometer screws.

All of the appliances available on the market comprise two parts:

a base ring of the appliance which is pressed against the eye around the cornea by an annular suction chamber; and a carriage carrying the blade and driven either by hand or automatically in slideways provided at the top portion of the fixing ring.

The opportunities for setting and adjusting those devices are rather few or they require additional parts. To adjust the thickness of the cornea disk, the distance between the cutting edge of the blade and a plate situated in front of the edge of the blade is adjusted. The plate serves to flatten the cornea before the blade acts on it. To act on the diameter of the disk to be sliced off, it is generally necessary to have a set of fixing rings of different sizes.

In addition, certain appliances provide a keratome with a vibrating blade which moves on its own between the ring and the cornea flattening plate. Other appliances propose a keratome in which the blade, which is inclined relative to the plane of cut, moves together with the cornea flattening plate. Under such circumstances, it is appropriate to insert and move the carriage carrying the cutting blade in guiding slideways of the ring, but that operation is difficult, awkward, and not ergonomic.

OBJECTS AND SUMMARY OF THE INVENTION

The present invention seeks to provide an appliance enabling a surgeon to proceed easily with all of the desirable adjustments and providing a choice between an appliance having a fixed flattening plate or an appliance having a flattening plate that moves with the cutting blade.

To this end, the invention provides a surgical appliance for slicing a sliver from the cornea, the appliance comprising:

a base comprising an annular suction chamber having an axis of symmetry, shaped to be pressed around the cornea of an eye, and provided with means for connection to a vacuum source;

a cornea-shaping element situated above the base and having a surface facing it; and a cutting blade displaceable in a plane situated between the surface of the shaping element and the base.

According to the main characteristic of the invention, the appliance includes a general support to which the base is coupled by means enabling its position relative to the support to be adjusted along the axis of symmetry of the annular chamber, and which is coupled to the cutting blade by means enabling its position relative to the general support to be adjusted along a direction parallel to the axis of symmetry of the annular chamber, and placed perpendicularly to said axis.

In this way, the keratome of the invention has a general support which constitutes a reference frame relative to which the elements of the keratome are movable and adjustable in position. It is thus possible to adjust individually all of the parameters concerning surgery. In particular, it may be observed that the blade support is guided by means which are not carried by the fixing ring. This constitutes an advantage of the invention compared with known microkeratomes. By construction, the spacing between the slideways carried by the ring determines the maximum diameter of the disk of cornea that can be sliced off, and in known devices, it is sometimes insufficient, e.g. for correcting hypermetropia. With the invention, this limit no longer exists and it is possible to slice off disks of larger diameter should the need arise.

In an embodiment, the general support comprises an upper ring forming means for holding the appliance, having an axis perpendicular to its plane, an arm extending down from said ring and converging on its axis, with the base being held in adjustable positions by the free end of the arm so that the axis of symmetry of the base coincides with the axis of the upper ring, and with an arm which extends outwards from the ring perpendicularly to its axis, on which arm there is slidably mounted a blade-carrying carriage which is adjustably extendable in a direction parallel to the axis of the ring.

By means of the general support, it is possible to provide an appliance in which either the cornea-shaping element is constituted by a lens applied in stationary but removable manner to the converging arm of the general support, or else said element is secured to the blade-carrying carriage, being situated thereon in front of the blade in the movement tending to bring it closer to the general axis of the support. Each of these dispositions naturally excludes the other, as explained in the description below.

When the blade is inclined forwards and downwards relative to its displacement plane, the shaping elements must be on board the blade-carrying carriage.

BRIEF DESCRIPTION OF THE DRAWINGS

Other characteristics and advantages of the invention appear from the description given below of various embodiments.

Reference is made to the accompanying drawings, in which.

MORE DETAILED DESCRIPTION

Figure 1:
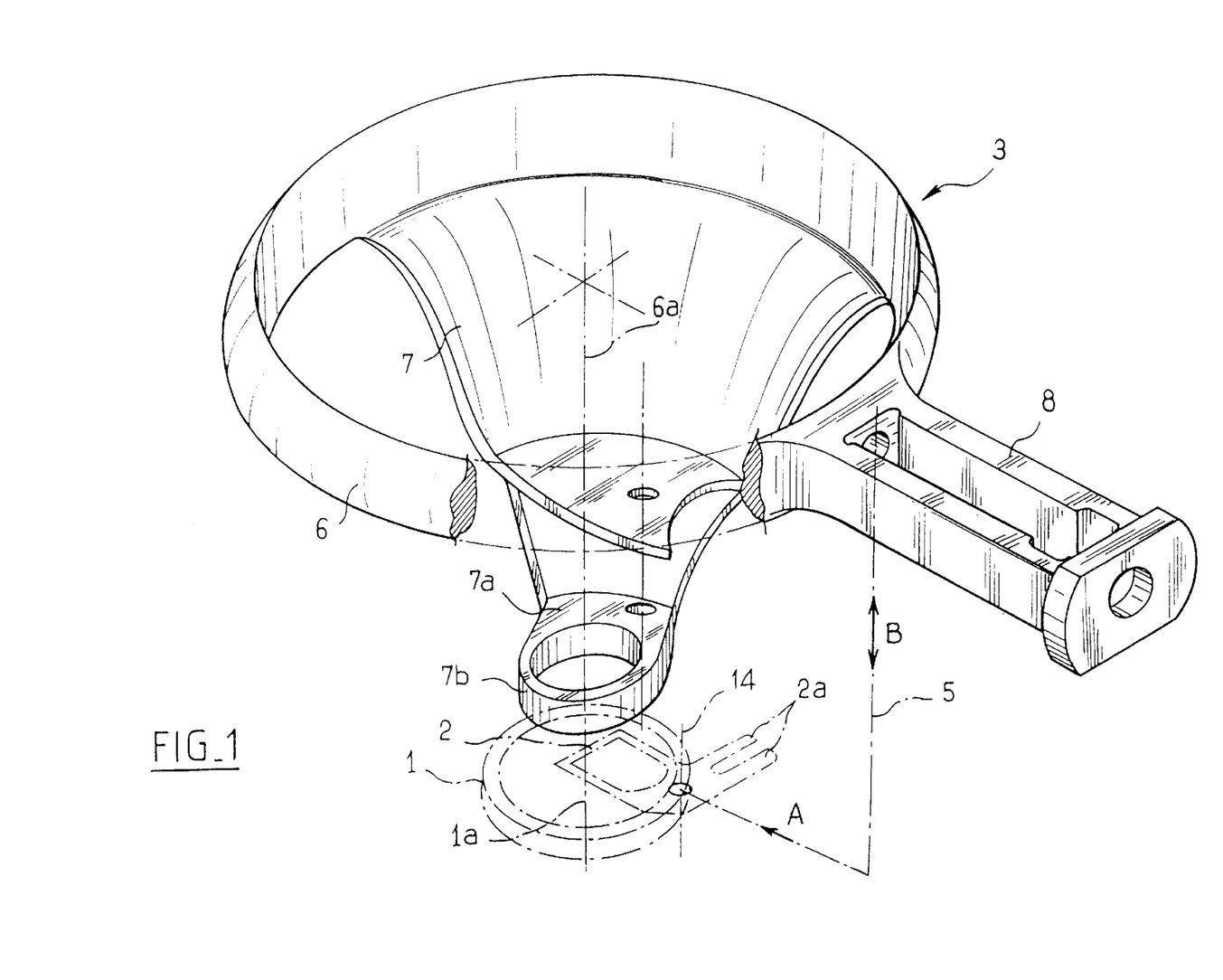
FIG. 1 is an outside view of an embodiment of the general support in accordance with the invention.

FIG. 1 is a diagram in which chain-dotted lines show the annular suction chamber forming the base of a keratome for surgery of the cornea. The annular chamber 1 is circularly symmetrical about an axis 1a.

In conventional manner, a keratome has a cutting blade 2 which is capable of oscillating in a plane perpendicular to the axis 1a of the base and lying above the base. It is explained below that this oscillation takes place along a circular arc, unlike in conventional devices where the oscillation is rectilinear. The cutting blade 2, when it is oscillating, is pushed in the direction A in its plane of oscillation towards the axis 1a, and it is in this direction that the disk of the cornea is sliced off. The blade is withdrawn in the direction opposite to that shown in the figure.

In the prior art, a blade carrier is slidably mounted in grooves above the suction chamber 1 and extending in the direction A so as to guide the movement of the blade relative to the projecting portion of the cornea inside the suction chamber. In general, blade 2 is preceded by a plate which flattens the cornea immediately prior to cutting, which plate is carried by the blade carrier. In other, less common, appliances the blade is inserted between the base and the tray for shaping and flattening the cornea which is fixed relative to the base while the blade is movable between them.

In the invention, a general support 3 is provided having connected thereto both the annular suction chamber 1 and the blade 2 in independent manner so that their positions relative to the support 3 and thus to one another are independently adjustable.

In this way, the annular chamber 1 can be adjusted in height along its axis 1a relative to the general support 3 by means represented by chain-dotted lines 4 and described below. The blade 2 is connected to the support 3 by means symbolized by chain-dotted lines 5 enabling both movement of the blade in direction A, i.e. perpendicularly to the axis 1a, and adjustment in a direction parallel to said axis.

In the embodiment shown, the general support has a top ring 6 which forms means for holding the appliance and having an axis 6a perpendicular to the its plane.

An arm 7 extends downwards from the ring, converging towards its axis 6a. The free end of the arm 7 has means for coupling the base of the keratome 1 in positions along the axis 6a which are such that the axis of symmetry 1a of the base coincides with the axis 6a of the upper ring 6. This arm 7 is preferably in the form of a sector of a conical wall which tapers towards its portion remote from its portion connected to the upper ring 6. In addition, the support has another arm 8 projecting out from the ring 6 perpendicularly to the axis 6a of the ring, said arm 8 constituting a member for supporting and guiding the sliding of a blade-carrier carriage represented by chain-dotted line 5, which carriage can thus be displaced perpendicularly to the axis 1a, the carriage being extendable in a direction parallel to said axis 1a, as shown by arrow B in FIG. 1.

Figure 2:
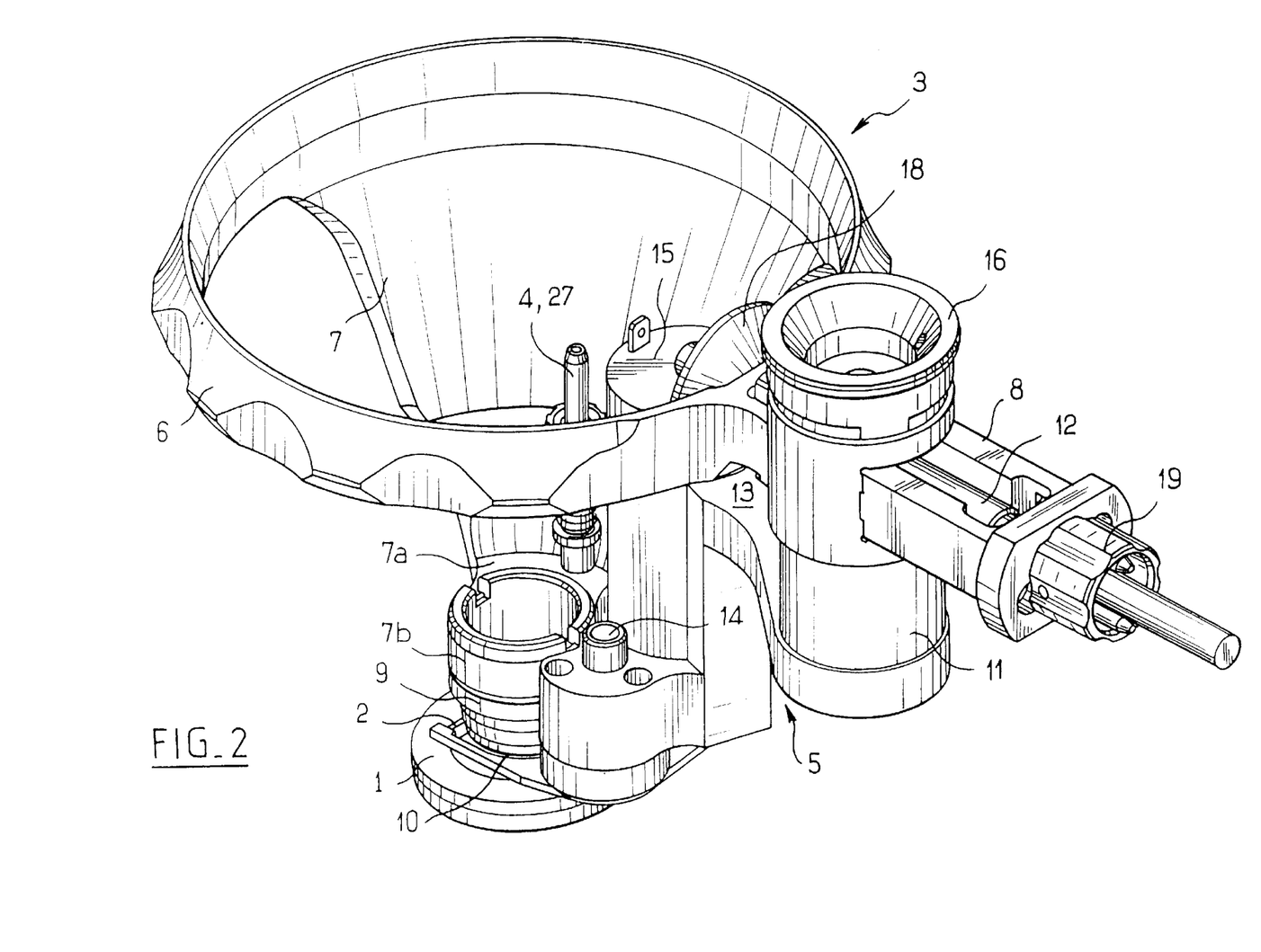
FIG. 2 is an outside view of a first embodiment of the appliance.

FIG. 2 shows the keratome of the invention together with all of its components. This figure includes the elements described above and given the same references. It will be observed in FIG. 1 that the end 7a of the arm 7 is shaped to form a kind of a ring 7b that is coaxial with the ring 6. The ring 7b is designed to receive a bush 9 that is closed at its bottom end by a transparent wall of surface 10 which constitutes an element for shaping the surface of the cornea, in general a cornea flattener, which is situated immediately above the base 1. The knife 2 operates between the surface 10 and the base 1. The base 1 can be adjusted in height relative to the surface 10 by means of a screw-and-nut system 4 which is described in greater detail with reference to FIG. 5.

In FIG. 2 it can be seen that the blade-carrier carriage 5 is quite complex in shape. In a nutshell it comprises a vertical shank 11 whose upper portion is engaged in the arm 8 and co-operates with a screw 12 in the manner of a screw-and-nut system so that rotating the screw 12 which is held longitudinally in position in the guide 8 causes the shank 11 to move in translation along the arm 8. The shank is of extendable length as described in greater detail with reference to FIG. 3. At the base of the shank 11, the carriage has a horizontal portion 13 directed towards the ring 6 under which it extends. This portion 13 forms the support firstly for a pivot axis 14 of the blade 2 and secondly for a motor 15 that drives said blade in oscillation about the axis 14. The motor 15 is fitted at the end of its outlet shaft with an eccentric cam which engages between the two tines of a fork 2a secured to the cutting blade 2, as shown in FIG. 1 which also shows the axis 14.

Figure 3:
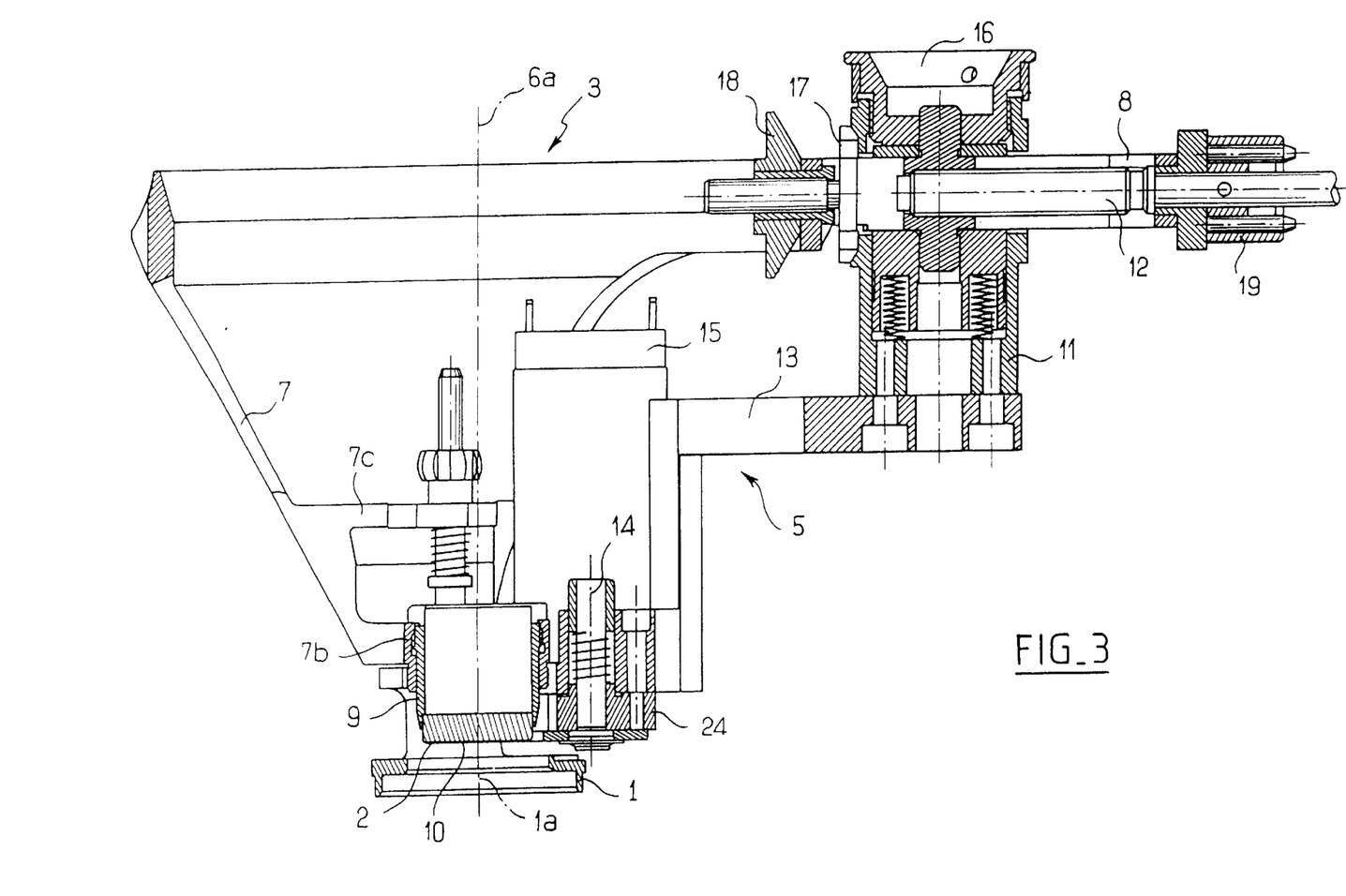
FIG. 3 is a section view of FIG. 2 on the cutting blade displacement direction.

FIG. 3 is a section view of FIG. 2 on a radial plane which naturally includes the axis 6a and which also includes the longitudinal axis of the arm 8 carrying the blade-carrier carriage 5. Various elements that are described above are to be found in this figure also, and they are given the same references. For example, in this figure, it can be seen that the shank 11 is suspended from a nut 16 which rests on the arm 8. It will be understood that by tightening or loosening the nut 16, the shank 11 is caused to move up or down relative to the arm 8, the shank 11 naturally being provided by openings through which the arm 8 passes and having sufficient clearance to cover an adjustment range that is satisfactory for the intended application. It will also be understood from this figure that by moving the shank 11 up or down relative to the arm 8, the distance between the blade 2 and the surface 10 carried by the end 7a of the arm 7 of the general support 3 is caused to vary. This makes it possible to adjust the thickness of the cornea disk that is to be sliced off.

It will also be observed in this figure that inside the arm 8 there is an abutment 17 whose position inside the arm is adjustable by means of a manual member 18. This abutment constitutes a limit on the stroke of the shank 11 and thus of the blade-carrier carriage 5 towards the axis 6a. The purpose of this abutment is to put a limit on the slicing off of the cornea disk so as to ensure that it is not completely detached from the cornea, should that be required by the operation.

Rotation of the screw 12 which is the drive screw for moving the blade-carrier carriage 5 towards and away from the axis 6a can be controlled manually by a control knob 19 situated at the end of the arm 8. It may also be controlled by a motor by coupling the screw 12 to a conventional drive cable or motor.

Figure 4:
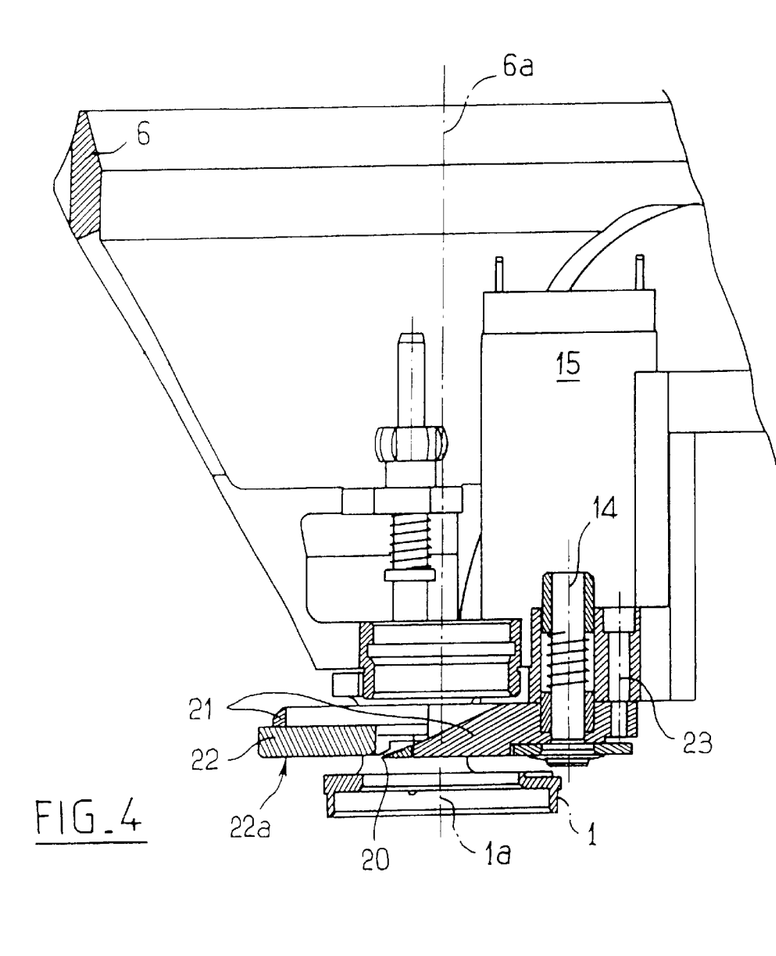
FIG. 4 shows a variant of the FIG. 3 appliance in which the cutting blade and the cornea-shaping element are displaceable together.

In FIG. 4, there can be seen a variant embodiment of the cutting device. In this case the knife has a blade 20 that is inclined relative to its displacement plane perpendicular to the axis 1a, 6a of the appliance, said blade naturally oscillating like the above-described blade 2 about the axis 14. Level with this blade, the carriage has a radial extension 21 for supporting a plate 22 which moves with the carriage and whose lower surface 22a constitutes the surface for flattening the cornea in front of the slicing blade, as in known keratomes. It would have been observed that to change from the keratome of FIG. 3 with an oscillating blade 2 that moves beneath a fixed plate to an inclined oscillating blade 20 which moves together with the plate for flattening the cornea, the operations required for making the changeover are simple. It suffices to remove the bush 4 which carries the surface 10 of the lower ring 7b of the general support 3 and to use the screws 23 to replace the lower element 24 of the blade carrier in FIG. 3 with the lower element 21 in FIG. 4. Under the conditions shown in FIG. 4, it is possible to adjust the thickness of the sliced-off cornea disk by changing the plate 22 and thus by changing the distance between its lower face 22a and the cutting blade.

Figure 4A:
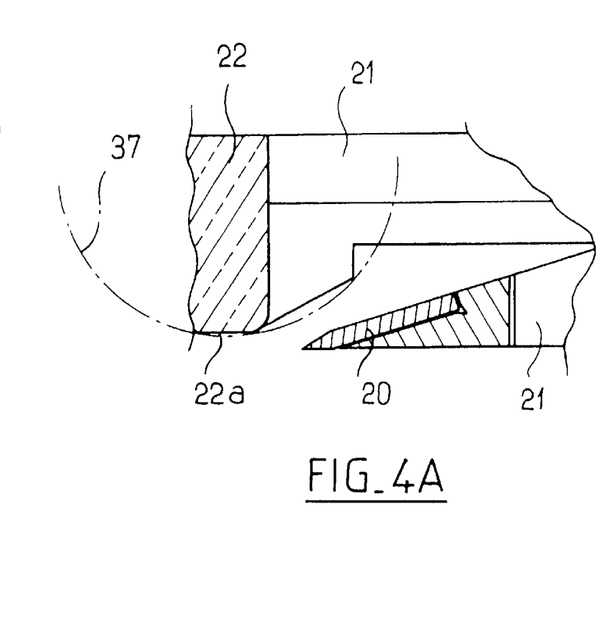
FIG. 4A is an enlarged view of a detail of the FIG. 4 variant.

FIG. 4A is a fragmentary view on a larger scale than FIG. 4 showing the cutting blade 20. Chain-dotted line 37 represents an element for shaping the cornea which differs from the flattening plate 22, thus showing that it is possible to implement either a cylindrical surface or a barrel-shaped surface that is has a non-linear generator line level with the knife 20 so as to accommodate various particular defects of the cornea, such as astigmatism. Naturally, under such circumstances, it is appropriate to orient the appliance about the axis 6a as a function of the topography of the cornea, and in particular the direction of the most highly curved meridian or the flattest meridian, when astigmatism is present.

Figures 4B, 7:
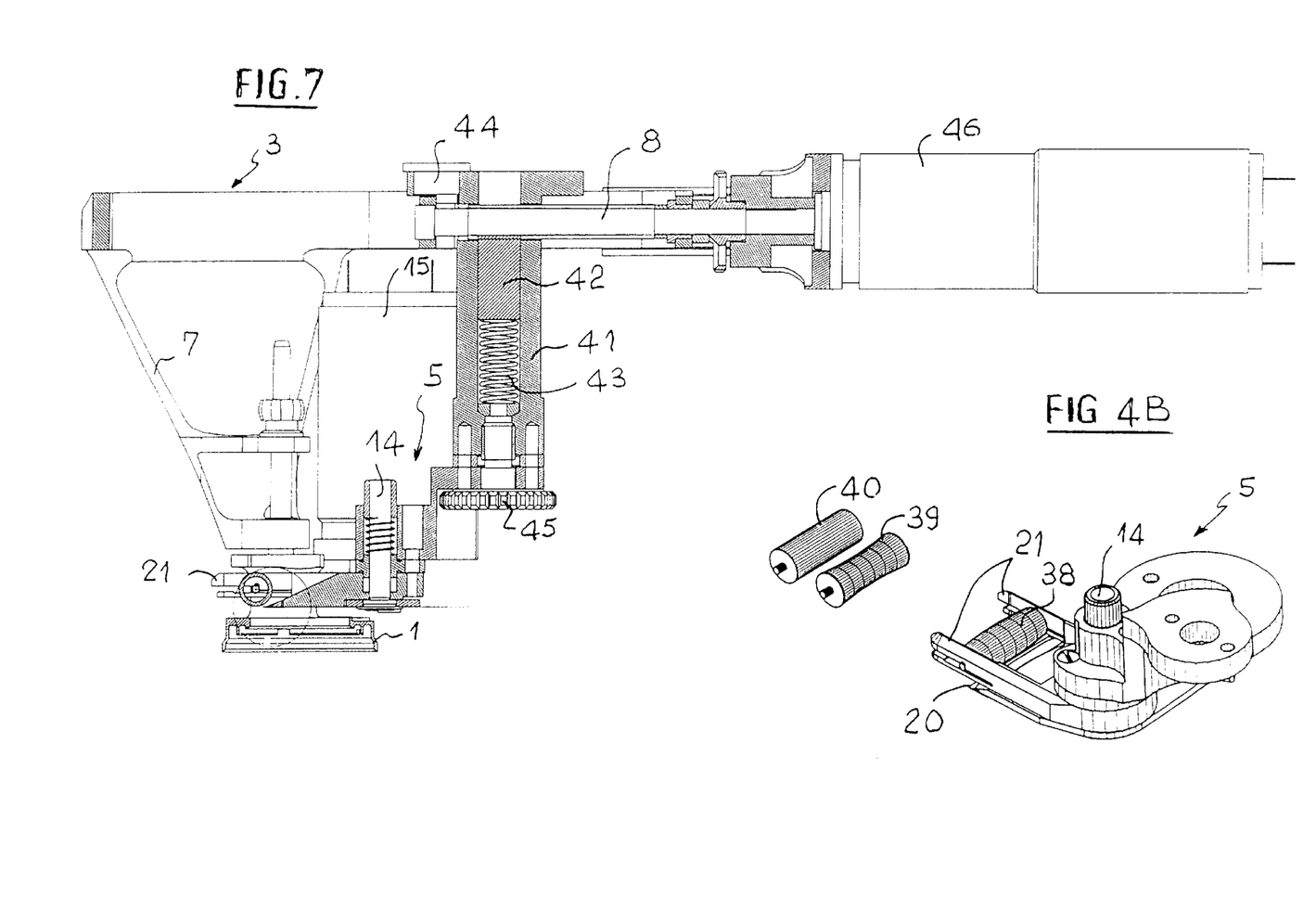
FIG. 4B shows different cornea-shaping elements for the variant of the FIG. 4.
FIG. 7 shows another variant of the invention.

FIG. 4B shows those different elements for shaping the cornea. The radial extension 21 comprises two arms which are slitted. The cornea shaping elements are in the form of rollers 38, 39, 40, interchangeable and each rotatable around an internal shaft, the ends of which being located in the slots of the arms of the extension 21. Roller 38 is barrel-shaped, roller 39 is shaped as a diabolo and roller 40 is cylindrical. The slots may also, of course receive the plate 22 instead of one of the rollers.

Figure 5:
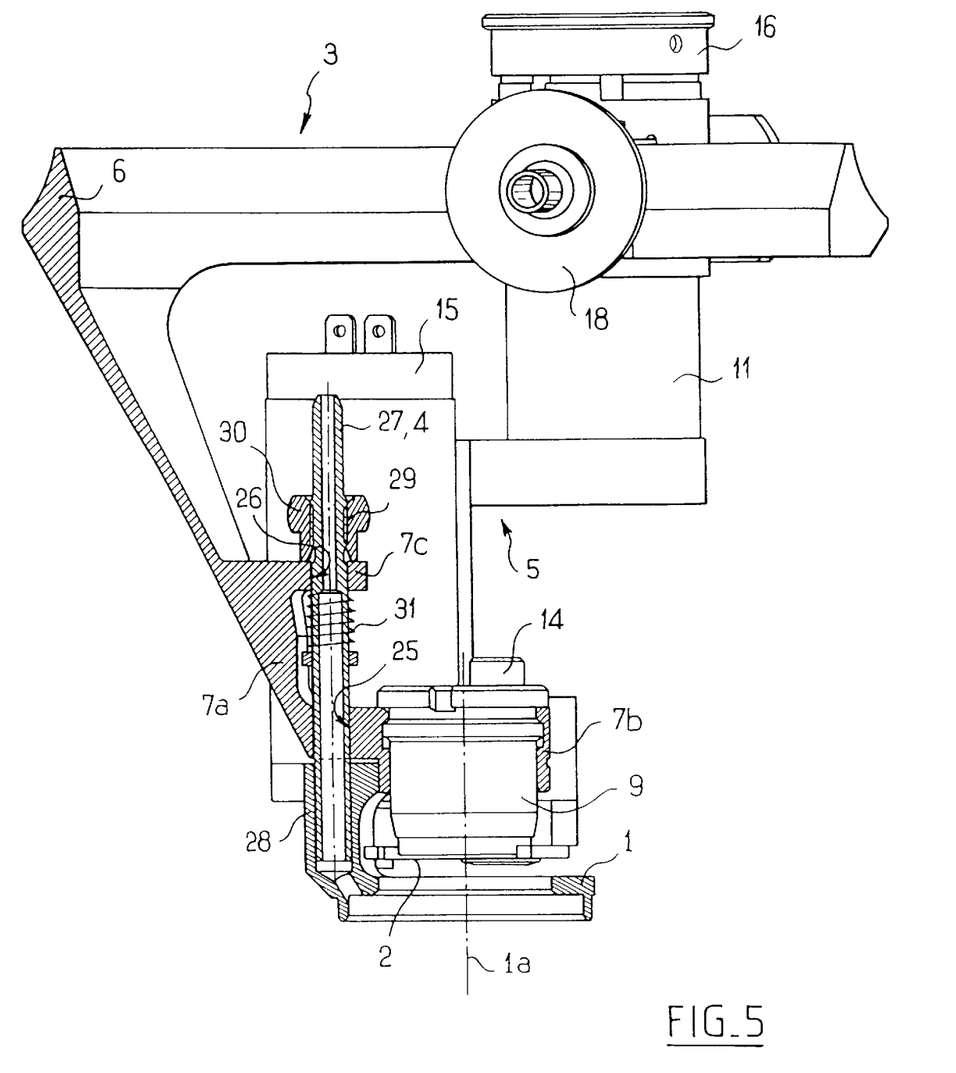
FIG. 5 is a radial section view through the appliance at the connection between the base and the general support.

FIG. 5 shows how the base 1 is coupled to the general support 3. At its end 7a, the arm 7 possesses not only its annular portion 7b for supporting the bush 9, but also a kind of intermediate gusset 7c, the end 7a of the gusset 7c being provided with orifices 25 and 26 that are in alignment, their axis being parallel to the axis 1a, and through which it is possible to insert a rod 27 secured to the base 1. Also, the base 1 is surmounted by a projection 28 which serves firstly to receive the rod 27 and secondly forms a kind of half-collar surrounding the bottom portion of the annular portion 7b of the arm 7, thereby constituting an anti-rotation guide for said base 1 relative to the axis of the rod 27.

In fact, the rod 27 is hollow and constitutes the endpiece for coupling the suction chamber constituted by the base 1 to a vacuum source. An upper portion of the rod 27 which extends beyond the gusset 7c is threaded at 29 so as to be capable of co-operating with a nut 30 which bears against the top surface of the gusset. In this way the base 1 is suspended from the arm 7. Turning the nut 30 serves to adjust the height of the base 1 relative to the arm 7, and a spring 31 engaged between the bottom surface 7c and a shoulder on the rod 27 serves to take up slack and is stiff enough to ensure that there is no vibration in operation concerning the position of the base 1 relative to the bush 9.

Figure 6:
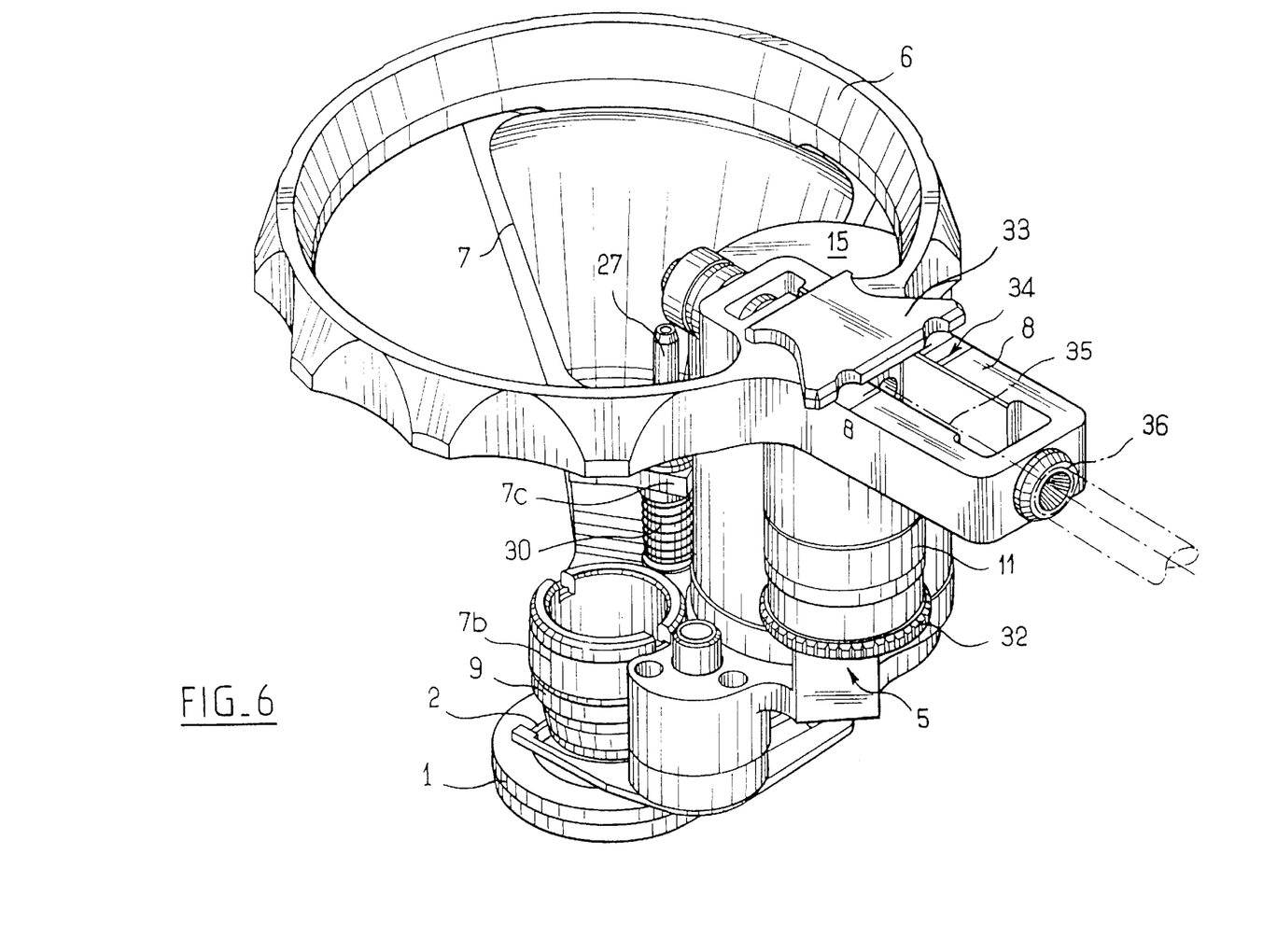
FIG. 6 is an outside view of a second variant of the invention.

In FIG. 6, there can be seen a variant embodiment of the keratome of the invention in which the portions described above are given the same references. In this variant, the knob for adjusting the position of the blade relative to the general support is situated beneath the arm 8 and is referenced 32. This makes it possible to put a cursor 33 on the arm, which cursor can move along a graduated scale 34, thereby providing an indication to the surgeon of the stroke of the blade for comparison with the diameter of the cornea disk so as to ensure that a hinge zone is conserved linking the disk to the cornea so that the disk remains as a flap which is easier to fold back down onto the plane of cut and to put back into position.

Similarly, in this implementation, the blade-carrying carriage 5 is not driven by means of a screw-and-nut system but is motor-driven by a means of a cable represented by chain-dotted line 35, one end of which is secured to the blade-carrying carriage 5 inside the arm 8, said cable being movable longitudinally inside a sheath 36 connected to the end of the arm 8 and extending beyond it. The cable is caused to slide relative to the sheath by means of a known motor acting on the other end of the sheath. This constitutes a conventional drive mechanism which has the advantage of controlling movement of the carriage 5 along the arm 8 in very regular manner.

In FIG. 7, it can be seen another variant embodiment in which the parts described above are given the same reference numbers. This embodiment is designed to cut the cornea with an inclined blade. Then it is no longer necessary to have the vertical shank adjustable in length as the shank described in FIG. 3. The shank 41 is directly in contact with the top of the arm 8. Inside of the shank, there is a piece 42 shaped as an half of a nut which is pushed permanently against the screw 12 by a spring 43. When the shank 41 is in contact with the adjustable stop 44, said half nut 42 escape of the thread of the screw 12 if it is rotating. The coupling there between is in that way disconnected.

A knob 45 performs the connection of the blade-carrier carriage to the shank 41. The stop 44 is different from the stop 17 of FIG. 3 because it is shaped as a cam surface like an eccentric for example.

It will be observed finally that a driving motor 46 is coupled to the screw 12 by means of disconnectable coupling means at the end of the arm 8.

I claim:

1. A surgical appliance for slicing a sliver from a cornea, the appliance comprising:

a base comprising an annular suction chamber having an axis of symmetry, shaped to be pressed against the sclera of an eye, and provided with means for connection to a vacuum source;

a cornea-shaping element situated above the base and having a surface facing it; and a cutting blade displaceable in a plane situated between the surface of the shaping element and the base;

the appliance including a general support to which the base is coupled by means enabling its position relative to the support to be adjusted along the axis of symmetry of the annular chamber, and which is coupled to the cutting blade by means enabling its position relative to the general support to be adjusted along a direction parallel to the axis of symmetry of the annular chamber, and placed perpendicularly to said axis.

2. An appliance according to claim 1, wherein the general support comprises an upper ring forming means for holding the appliance, having an axis perpendicular to its plane, an arm extending down from said ring and converging on its axis, with the base being held in adjustable positions by the free end of the arm so that the axis of symmetry of the base coincides with the axis of the upper ring, and with an arm which extends outwards from the ring perpendicularly to its axis, on which arm there is slidably mounted a blade-carrying carriage which is adjustably extendable in a direction parallel to the axis of the ring.

3. An appliance according to claim 2, wherein the cornea-shaping element is constituted by a lens fixed in stationary but removable manner to the converging arm of the general support.

4. An appliance according to claim 2, wherein the shaping elements is secured to the blade-carrying carriage ahead of the blade in the movement bringing the blade towards the axis of the general support.

5. An appliance according to claim 4, wherein the blade slopes forwards and downwards in its displacement plane.

6. An appliance according to claim 1, wherein the support includes an adjustable abutment for limiting the stroke of the blade-carrying carriage towards the axis.

7. An appliance according to claim 1, wherein the cutting blade is slidably mounted in its plane of displacement relative to the blade-carrying carriage, the carriage carrying a drive member for actuating the blade via an eccentric cam.

8. An appliance according to claim 1, wherein the means for connection to the annular suction chamber of the base comprise a cylindrical endpiece forming the screws of a screw-and-nut system constituting the member for adjusting the position of the base relative to the general support.

9. An appliance according to claim 4, wherein the element for shaping the cornea possesses a surface facing the base which is cylindrical or barrel-shaped.

10. An appliance according to claim 2, wherein the blade-carrying carriage is coupled to a member for driving it along the arm, which member is constituted by a cable movable in translation inside a sheath that is itself coupled to the arm and constitutes an extension thereof.

11. An appliance according to claim 2, wherein the blade-carrying carriage is coupled to a driving member which is constituted by a screw rotatably mounted in said arm and coupled to a driving motor at the end of said arm.

12. An appliance according to claim 11 wherein the screw is meshing with a half nut piece which is fixed to the blade-carrying carriage.

* * * * *